(12) United States Patent
Miller

(10) Patent No.: US 11,026,846 B2
(45) Date of Patent: Jun. 8, 2021

(54) ELBOW COMPRESSION WRAP AND CORRESPONDING METHODS

(71) Applicant: Medline Industries, Inc., Mundelein, IL (US)

(72) Inventor: Christopher Miller, Chicago, IL (US)

(73) Assignee: Medline Industries, Inc., Northfield, IL (US)

( * ) Notice: Subject to any disclaimer, the term of this patent is extended or adjusted under 35 U.S.C. 154(b) by 799 days.

(21) Appl. No.: 15/285,737

(22) Filed: Oct. 5, 2016

(65) Prior Publication Data
US 2018/0092782 A1    Apr. 5, 2018

(51) Int. Cl.
*A61F 13/10*        (2006.01)

(52) U.S. Cl.
CPC .................................. *A61F 13/108* (2013.01)

(58) Field of Classification Search
CPC .. A61F 5/01; A61F 5/013; A61F 5/106; A61F 5/109; A61F 5/0118; A61F 13/00; A61F 13/10; A61F 13/101; A61F 13/107; A61F 13/06; A61F 13/061; A61F 13/064; A61F 13/066; A61F 13/104; A61F 13/08; A61F 13/085; A61F 5/0109; A61F 5/0111; A61F 13/062; A61F 13/108; A61F 15/004; A61F 5/30; A61F 5/32; A61F 5/34; A61F 13/0273; A61F 13/102; A61F 2013/00119; A61F 2013/0028; A61F 7/02
USPC ............................ 602/41, 60, 61, 62, 63, 75
See application file for complete search history.

(56) References Cited

U.S. PATENT DOCUMENTS

| | | | | |
|---|---|---|---|---|
| 3,858,881 | A | * | 1/1975 | Hurwitz ................. A63B 69/38 473/229 |
| 4,027,666 | A | | 6/1977 | Marx |
| 5,165,402 | A | * | 11/1992 | McCoy ..................... A61F 7/02 602/2 |
| 5,372,575 | A | * | 12/1994 | Sebastian ................ A61F 5/012 128/DIG. 20 |
| 5,624,388 | A | | 4/1997 | Lehr |
| D390,961 | S | | 2/1998 | Walker et al. |
| 6,149,617 | A | | 11/2000 | McNally et al. |
| 6,338,722 | B1 | * | 1/2002 | Barbe-Vicuna ......... A61F 13/10 602/62 |
| 6,398,749 | B1 | | 6/2002 | Slautterback |
| 6,863,657 | B1 | * | 3/2005 | Clements .............. A61F 5/0106 602/23 |
| 7,229,426 | B2 | | 6/2007 | Weaver, II et al. |

(Continued)

OTHER PUBLICATIONS

"DashSport Elbow System", Amazon.com; viewed on Aug. 11, 2016; https://www.amazon.com/DashSport-Elbow-System-Compression-Complete/dp/B00WNSXFX6.

*Primary Examiner* — Ophelia A Hawthorne
(74) *Attorney, Agent, or Firm* — Philip H. Burrus, IV

(57) ABSTRACT

A compression wrap (100) includes an elongated wrap body (101) extending from a first end (102) to a distal end (103). A fastening tab (116) is coupled to a first major face (205) of the elongated wrap body at the first end. A fastening loop (118) is coupled to the first major face of the elongated wrap body at the distal end. A compression pad (106) is disposed along a second major face (105) of the elongated wrap body between the first end and the distal end. A stretchable layer (108) straddles the compression pad such that the stretchable layer and a portion (208) of the elongated wrap body comprising the compression pad define a stretchable sleeve (303).

20 Claims, 6 Drawing Sheets

(56) References Cited

U.S. PATENT DOCUMENTS

| | | | |
|---|---|---|---|
| 8,628,488 B2* | 1/2014 | Serola | A61B 17/1325 128/846 |
| 2003/0032912 A1* | 2/2003 | Weaver, II | A61F 13/108 602/62 |
| 2015/0136821 A1* | 5/2015 | Sorenson | A45F 5/00 224/222 |
| 2016/0000612 A1* | 1/2016 | Cox | A61F 13/085 602/62 |
| 2016/0362824 A1* | 12/2016 | Ausen | B29D 28/00 |

* cited by examiner

ELBOW COMPRESSION WRAP AND CORRESPONDING METHODS

BACKGROUND

Technical Field

This disclosure relates generally to therapeutic devices, and more particularly to compression devices.

Background Art

Athletes are sometimes prone to injury from overexertion. Illustrating by example, tennis players can suffer from tendon damage when their forearms are moved repeatedly in the same manner under load and stress. This motion can cause damage to tendon attachments and muscles, which can result to pain, inflammation, and reduced range of motion. This injury is so prevalent that it is referred to as lateral epicondylitis, which is sometimes colloquially known as "tennis elbow." While called "tennis elbow," the affliction can befall golfers as well, and can even affect labors who make continuous motions such as turning screws or hammering nails.

Wrap devices are sometimes used to treat tennis elbow. Such wrap devices encircle the arm near the elbow to create pressure and to support the muscles and tendons of the arm. However, prior art wrap devices are difficult for a person to apply to an arm with a single hand. It would be advantageous to have an improved device that was easier to don.

Figure 1:
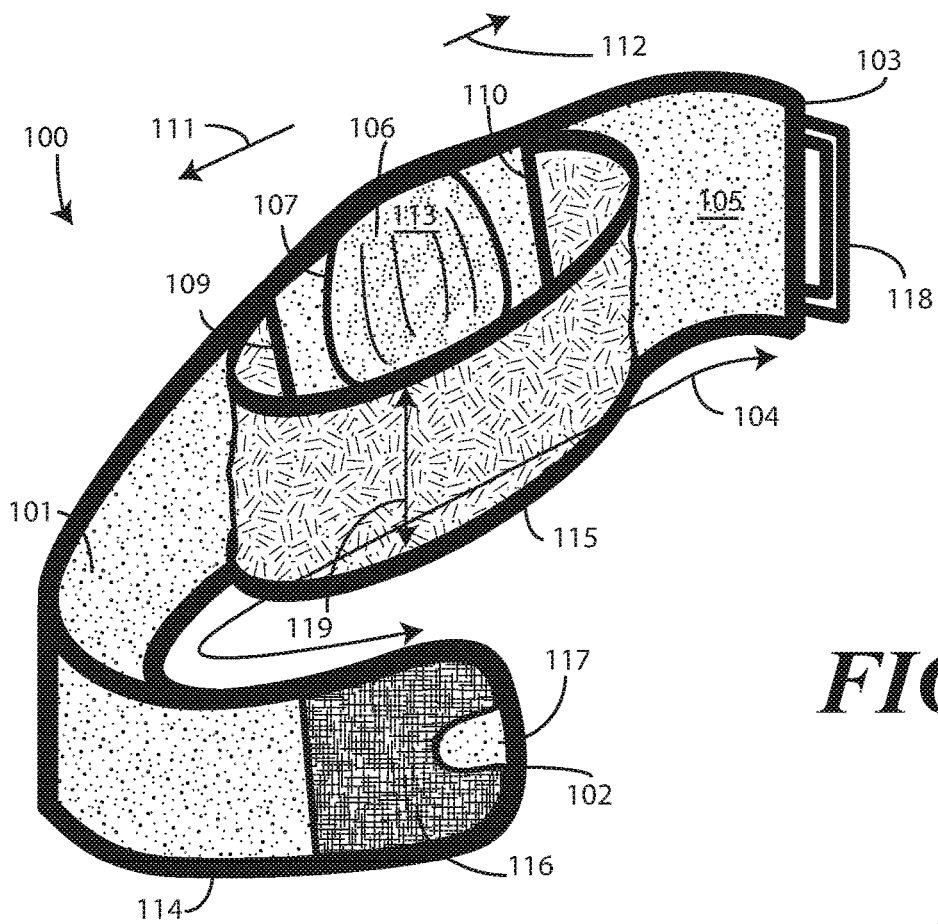
FIG. 1 illustrates a first perspective view of one explanatory compression wrap in accordance with one or more embodiments of the disclosure.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present disclosure.

DETAILED DESCRIPTION OF THE DRAWINGS

Embodiments of the disclosure are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." In this document, relational terms such as first and second, top and bottom, and the like may be used solely to distinguish one entity or action from another entity or action without necessarily requiring or implying any actual such relationship or order between such entities or actions. Further, it is expected that one of ordinary skill, notwithstanding possibly significant effort and many design choices motivated by, for example, available time, current technology, and economic considerations, when guided by the concepts and principles disclosed herein will be readily capable of building and using compression devices in accordance with embodiments of the disclosure with minimal experimentation.

As used herein, components may be "coupled" or "operatively coupled" when information can be sent between such components, even though there may be one or more intermediate or intervening components between, or along the connection path. The terms "substantially" and "about" are used to refer to dimensions, orientations, or alignments inclusive of manufacturing tolerances. Thus, a "substantially orthogonal" angle with a manufacturing tolerance of plus or minus two degrees would include all angles between 88 and 92, inclusive. Also, reference designators shown herein in parenthesis indicate components shown in a figure other than the one in discussion. For example, talking about a device (10) while discussing figure A would refer to an element, 10, shown in figure other than figure A.

Embodiments of the disclosure provide a compression wrap having a compression pad disposed along an elongated wrap member for applying therapeutic pressure to the limb of a wearer. In one or more embodiments, a stretchable layer straddles the compression pad with a first end coupled to the elongated wrap member to one side of the compression pad and another end coupled to the elongated wrap member to another side of the compression pad. In so doing, the stretchable layer and the portion of the elongated wrap member comprising the compression pad define a sleeve that enables a user to don the compression device without having to leverage it against their body, or to alternatively receive assistance from another person. In one or more embodiments, the sleeve defined by the stretchable layer and the portion of the elongated wrap member comprising the compression pad wraps around the user's forearm or other limb portion so that their free hand is available to secure the elongated wrap member with little effort involved.

In one embodiment, a compression wrap comprises an elongated wrap body extending from a first end to a distal end. A fastening tab can then be coupled to a first major face of the elongated wrap body at the first end. In one or more embodiments, a fastening loop is then coupled to the first major face of the elongated wrap body at the distal end.

In one or more embodiments, a compression pad is then disposed along a second major face of the elongated wrap body between the first end of the elongated wrap body and the distal end of the elongated wrap body. A stretchable layer then straddles the compression pad. In one or more embodiments, this occurs when a first stretchable layer end of the stretchable layer is coupled to the second major face of the elongated wrap body to a first side of the compression pad, while a second stretchable layer end of the stretchable layer is coupled to the second major face of the elongated wrap body to a second side of the compression pad.

This straddled configuration results in the stretchable layer defining a partially circular portion of a sleeve. A portion of the elongated wrap body comprising the compression pad forms a complementary partially circular portion of the sleeve. The two complementary partially circular portions of the sleeve define a stretchable sleeve into which one may insert an arm or limb. The elongated wrap body can then be tightened about the stretchable sleeve using the fastening tab.

Figure 2:
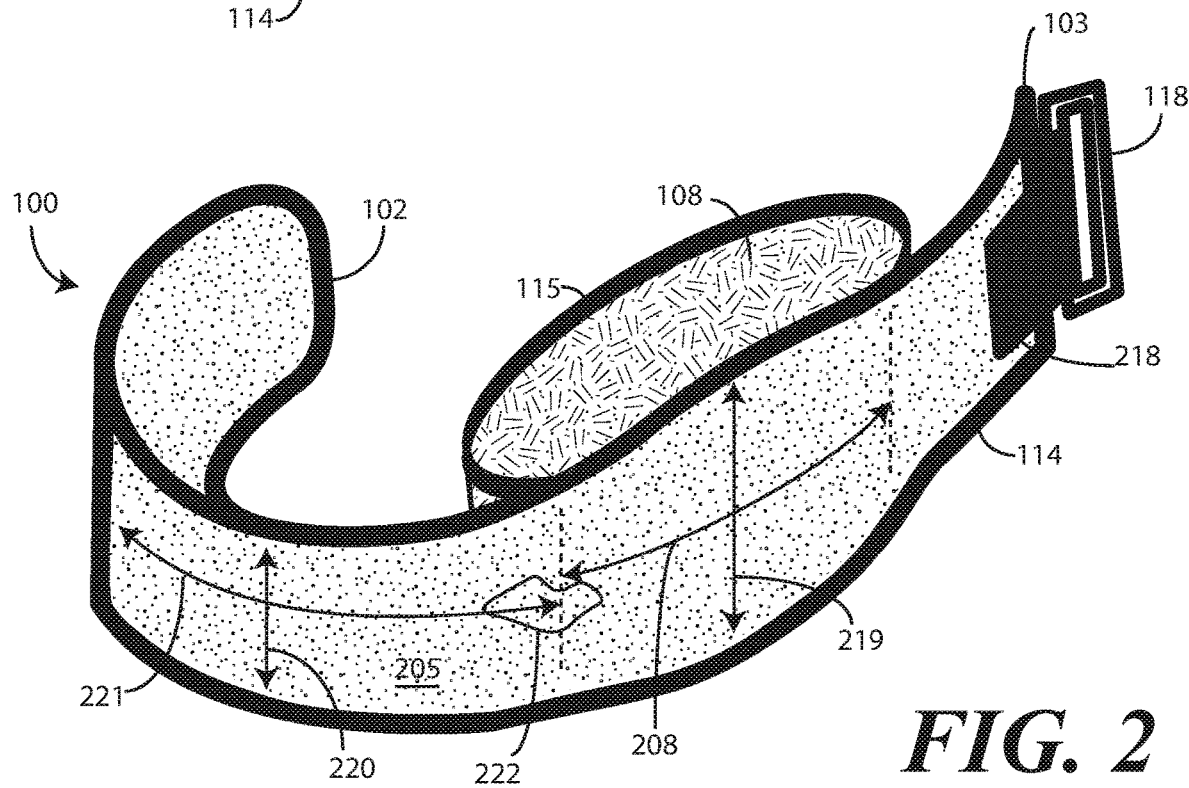
FIG. 2 illustrates another perspective view of one explanatory compression wrap in accordance with one or more embodiments of the disclosure.
Figure 3:
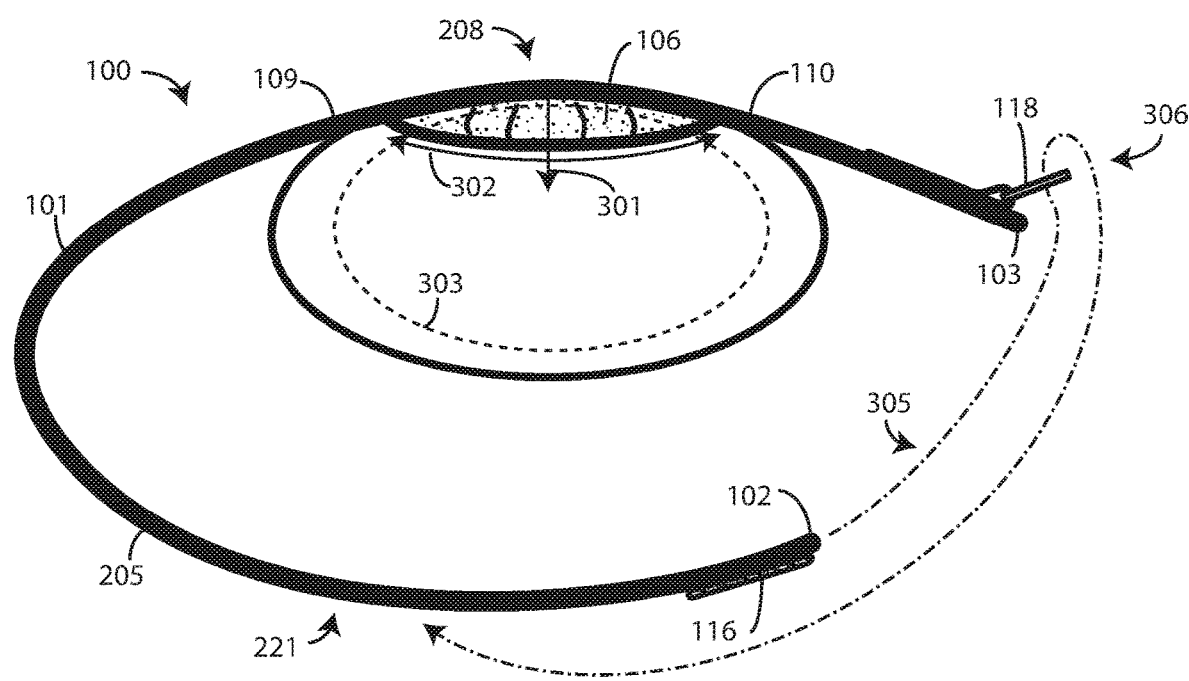
FIG. 3 illustrates a top plan view of one explanatory compression wrap in accordance with one or more embodiments of the disclosure.

Turning now to FIGS. 1-3, illustrated therein is one example of a compression wrap 100 configured in accordance with one or more embodiments of the disclosure. In one embodiment, the compression strap comprises an elongated wrap body 101 extending from a first end 102 to a distal end 103. In one or more embodiments, the elongated wrap body 101 is elastically stretchable. For example, the length 104 of the elongated wrap body 101 will increase when the first end 102 and the distal end 103 are pulled away from each other.

In one or more embodiments, the elongated wrap body 101 is manufactured from multiple layers of material. Illustrating by example, in one embodiment a first layer of material defines a first major face 205 of the elongated wrap body 101, while a second layer of material defines a second major face 105 of the elongated wrap body 101. In one or more embodiments, the layers of material defining the first major face 205 and the second major face 105 are manufactured from a blend of neoprene and nylon.

In one or more embodiments, a compression pad 106 is disposed along the second major face 105 of the elongated wrap body 101 between the first end 102 and the distal end 103. In one embodiment, the compression pad 106 is manufactured from compressible foam. However, in other embodiments the compression pad 106 can be a liquid filled pillow, air filled pillow, textile filled pillow, hard rubber pad, or soft rubber pad. Still other materials suitable for manufacturing the compression pad 106 will be obvious to those of ordinary skill in the art having the benefit of this disclosure.

In one embodiment, the outward surface 113 of the compression pad 106 is smooth. In other embodiments, the outward surface 113 of the compression pad 106 is textured to apply differing amounts of pressure to a user's limb to achieve dynamic therapeutic effects.

In one or more embodiments, the compression pad 106 is disposed between the first layer of material defining the first major face 205 of the elongated wrap body 101 and the second layer of material defining the second major face 105 of the elongated wrap body 101. In one or more embodiments, the compression pad 106 is coupled beneath the second layer of material defining the second major face 105 of the elongated wrap body 101 by stitching 107 so as to extend 301 distally from the elongated wrap body 101. In this manner, the compression pad 106 defines a protrusion extending 301 from one side of the elongated wrap body 101 and not the other. In the illustrative embodiment of FIGS. 1-3, the compression pad 106 defines an ovular perimeter 302 along the second major face 105 of the elongated wrap body 101.

In one or more embodiments, a stretchable layer 108 is coupled to the elongated wrap body 101. In one or more embodiments, the stretchable layer 108 straddles the compression pad 106 with a first stretchable layer end 109 coupled to the second major face 105 of the elongated wrap body 101 to a first side 111 of the compression pad 106 and a second stretchable layer end 110 coupled to the second major face 105 of the elongated wrap body 101 to a second side 112 of the compression pad 106. By straddling the compression pad 106 in this manner, the stretchable layer 108 and a portion 208 of the elongated wrap body 101 comprising the compression pad 106 define a stretchable sleeve 303. In the illustrative embodiment of FIGS. 1-3, the stretchable sleeve 303 is disposed closer to the distal end 103 of the elongated wrap body 101 than to the first end 102 of the elongated wrap body 101.

In one embodiment, the stretchable layer 108, which is elastic so as to be stretchable, is manufactured from a common material as that of the elongated wrap body 101. For example, in one embodiment the stretchable layer 108 is manufactured from a blend of neoprene and nylon. However, in other embodiments, the stretchable layer 108 and the elongated wrap body 101 are manufactured from different materials. For instance, in another embodiment the stretchable layer 108 can be manufactured from a combination of neoprene and nylon while the elongated wrap body 101 is manufactured from tricot. Other materials suitable for manufacturing either the stretchable layer 108 or the elongated wrap body 101 will be obvious to those of ordinary skill in the art having the benefit of this disclosure.

A border layer 114 of material can be applied to edges of the elongated wrap body 101 in one embodiment. For example, an additional layer of material can be overlaid to span an edge of the first major face 205 and the second major face 105 so as to define a border to prevent raveling and fraying. Similarly, a border layer 115 of material can be applied to edges of the stretchable layer 108 in a similar manner. In one embodiment, both the border layer 114 of material defining an edge of the elongated wrap body 101 and the border layer 115 defining an edge of the stretchable layer 108 are elastic and are stretchable.

In one embodiment, a fastening tab 116 is coupled to the elongated wrap body 101. In the illustrative embodiment of FIGS. 1-3, the fastening tab 116 is coupled to the first major face 205 of the elongated wrap body 101 at the first end 102. In one embodiment, the fastening tab 116 comprises a hook fastener. For example, the fastening tab 116 can be manufactured from VELCRO.SUP™ or another hook-style fastener. In one embodiment, the fastening tab 116 defines a concave recess 117 along the first end of the elongated wrap body 101. This allows a user to grab the first end 102 of the elongated wrap body 101 by placing a finger in the concave recess 117, thereby grasping the first major face 205 and the second major face 105 of the elongated wrap body 101 without touching the fastening tab 116.

In one or more embodiments, a fastening loop 118 is coupled to the elongated wrap body 101. In the illustrative embodiment of FIGS. 1-3, the fastening loop 118 is coupled to the first major face 205 of the elongated wrap body 101. In one embodiment, a layer of material 218, such as a nylon strap, is stitched to the first major face 205 and encircles a portion of the fastening loop 118 as shown in FIG. 2. Other techniques for attaching the fastening loop 118 to the elongated wrap body 101 will be obvious to those of ordinary skill in the art having the benefit of this disclosure. In one embodiment, the fastening loop 118 is manufactured from a rigid material such as plastic.

Figure 4:
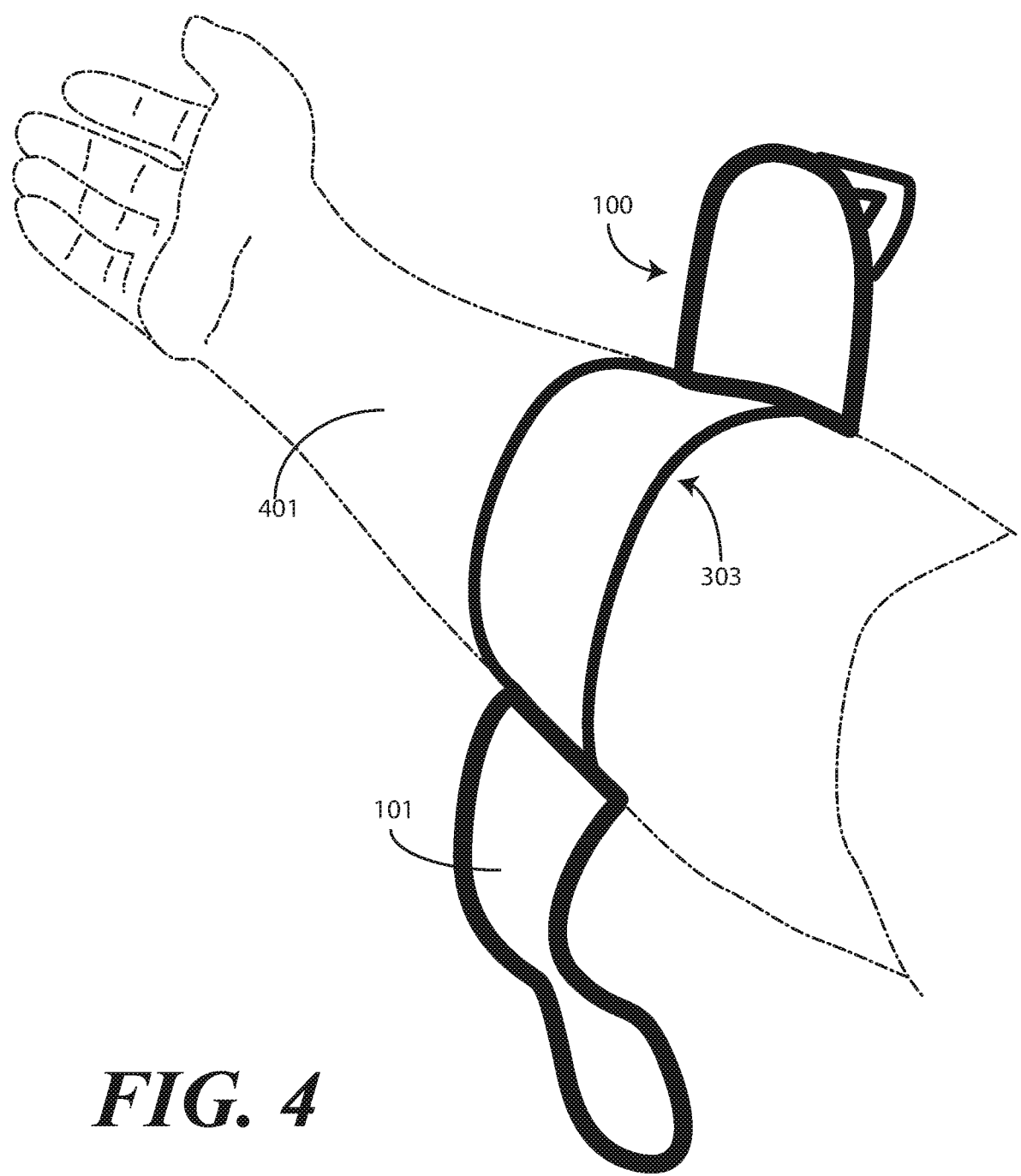
FIG. 4 illustrates a first step of donning an explanatory compression wrap in accordance with one or more embodiments of the disclosure.

As best seen by comparing FIGS. 1 and 2, in one embodiment the stretchable layer 108 defines a width 119 that is less than another width 219 of the portion 208 of the elongated wrap body 101 comprising the compression pad 106. In one embodiment, the width 119 of the stretchable layer 108 is less than the narrowest width 220 of the elongated wrap body 101. As will be shown in more detail below with reference to FIGS. 4-6, in one or more embodiments the elongated wrap body 101 is configured to wrap about the stretchable layer 108. By making the width 119 of the stretchable layer 108 less than the narrowest width 220 of the elongated wrap body 101, this allows the elongated wrap body 101 to conceal the stretchable layer 108 when the elongated wrap body 101 wraps about the stretchable layer 108.

In one or more embodiments, the width 219 of the portion 208 of the elongated wrap body 101 comprising the compression pad 106 is greater than the narrowest width 220 of the elongated wrap body 101. Moving from the first end 102 of the elongated wrap body 101 to the distal end 103, in one embodiment the width transitions from the narrowest width 220 to the width 219 of the portion 208 of the elongated wrap body 101 comprising the compression pad 106 and then tapers again toward the distal end 103. For example, in one embodiment the portion 208 of the elongated wrap body 101 comprising the compression pad 106 is wider than another portion 221 of the elongated wrap body 101 disposed between the portion 208 of the elongated wrap body 101 comprising the compression pad 106 and the fastening tab 116. In another embodiment, the width transitions from the narrowest width 220 to the width 219 of the portion 208 of the elongated wrap body 101 comprising the compression pad 106 and does not get narrower moving toward the distal end 103 of the elongated wrap body 101. Other shapes for the elongated wrap body 101 will be obvious to those of ordinary skill in the art having the benefit of this disclosure.

In one or more embodiments, the first major face 205 of the elongated wrap body 101 comprises one or more loops 222 engageable by the fastening tab 116. For example, where the first major face 205 is manufactured from a combination of neoprene and nylon, the one or more loops 222 are naturally formed by the weaving process. Accordingly, the fastening tab 116 can engage these one or more loops 222 by simply being pressed against the first major face 205 of the elongated wrap body 101. In another embodiment, a loop fastener can be attached to the first major face 205.

As best shown in FIG. 3, in one or more embodiments the portion 221 of the elongated wrap body 101 disposed between the portion 208 of the elongated wrap body 101 comprising the compression pad 106 and the fastening tab 116 is insertable 305 through the fastening loop 118. In one embodiment, the first major face 205 of the elongated wrap body 101 is then foldable 306 against itself after the portion 221 of the elongated wrap body 101 disposed between the portion 208 of the elongated wrap body 101 comprising the compression pad 106 and the fastening tab 116 is inserted through the fastening loop 118. This allows the fastening tab 116 to engage the one or more loops 222 of the elongated wrap body 101 to secure the elongated wrap body 101 about the stretchable layer 108.

As noted above, embodiments of the disclosure advantageously allow a user to don the compression wrap 100 without "pinching" the elongated strap member between an arm and their torso, or alternatively without having to avail themselves of third party assistance. Illustrating by example, turning now to FIG. 4, when the compression wrap 100 is donned, a user places their arm 401 through the stretchable sleeve 303 and positions the compression wrap 100 at an appropriate location along the arm 401. The stretchable sleeve 303 then retains the compression wrap 100 in position. This frees the user's other hand to fix the elongated wrap body 101 about the stretchable sleeve 303.

Figure 5:
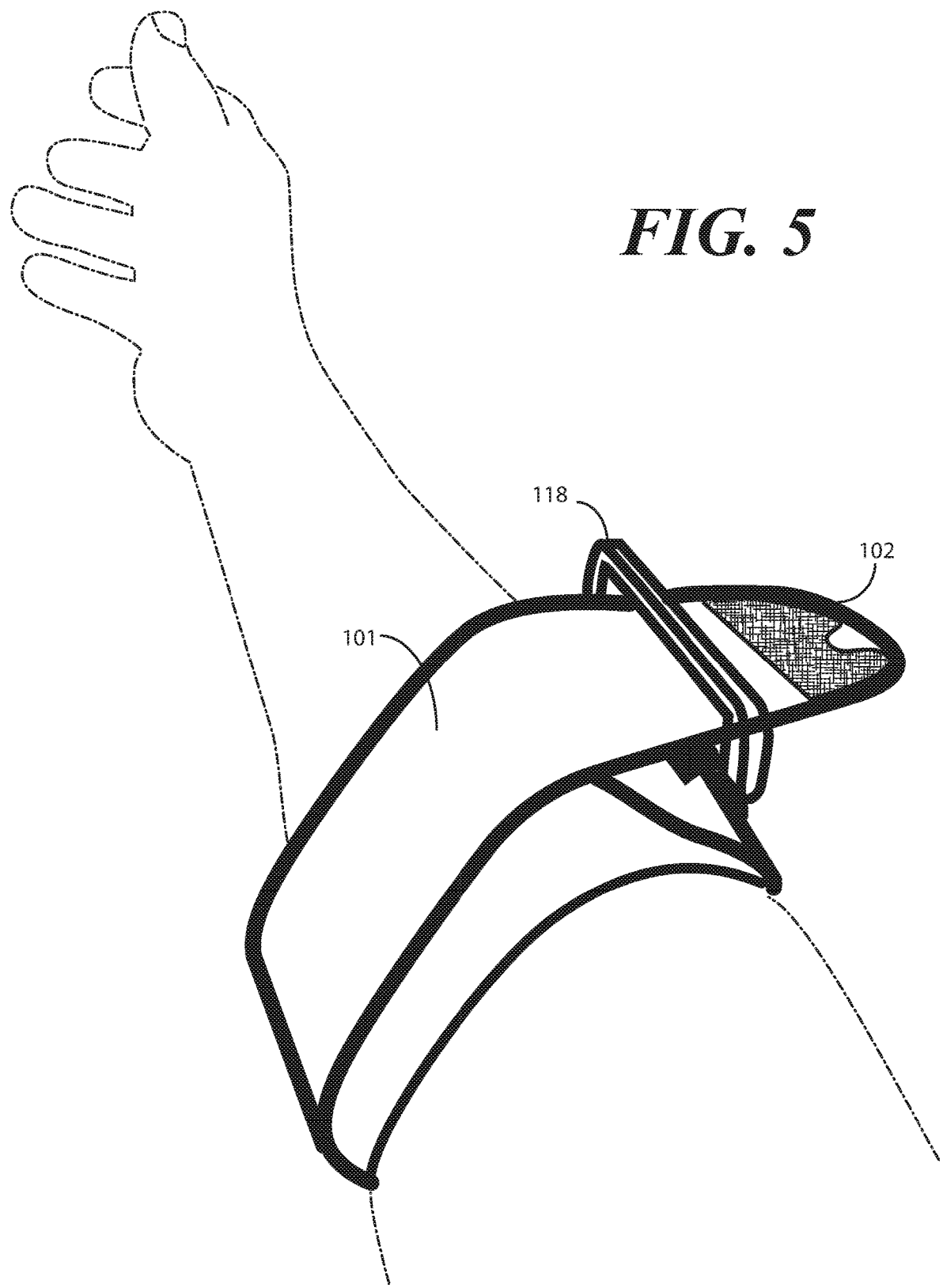
FIG. 5 illustrates another step of donning an explanatory compression wrap in accordance with one or more embodiments of the disclosure.
Figure 6:
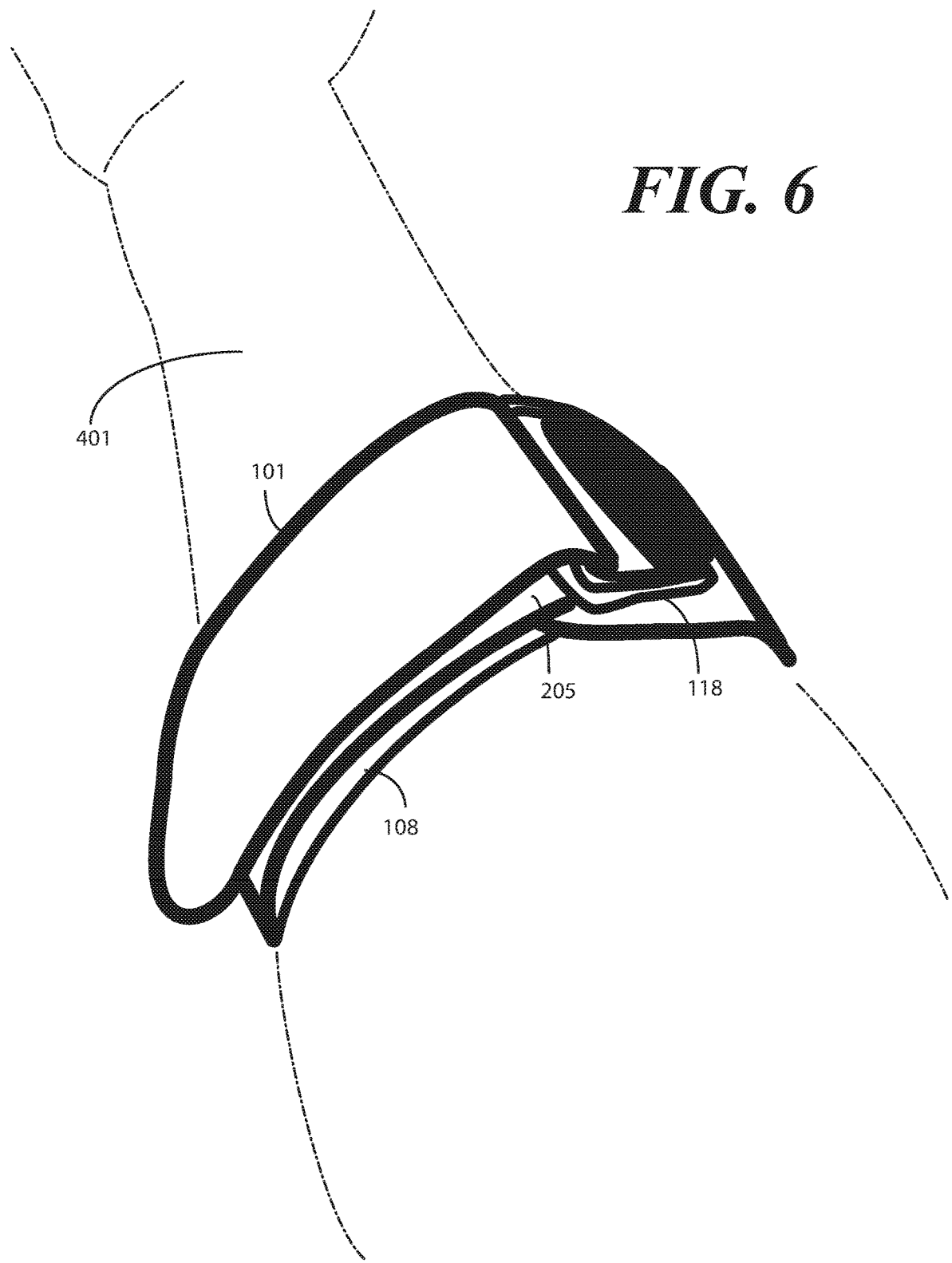
FIG. 6 illustrates another step of donning an explanatory compression wrap in accordance with one or more embodiments of the disclosure.

Turning now to FIG. 5, the first end 102 of the elongated wrap body 101 can then be inserted through the fastening loop 118. Turning to FIG. 6, the first major face 205 of the elongated wrap body 101 is then folded back across the fastening loop 118 against itself. This allows the fastening tab (116) to engage the one or more loops (222) of the elongated wrap body 101 to secure the elongated wrap body 101 about the stretchable layer 108 to provide compression therapy to the user's arm 401.

Figure 7:
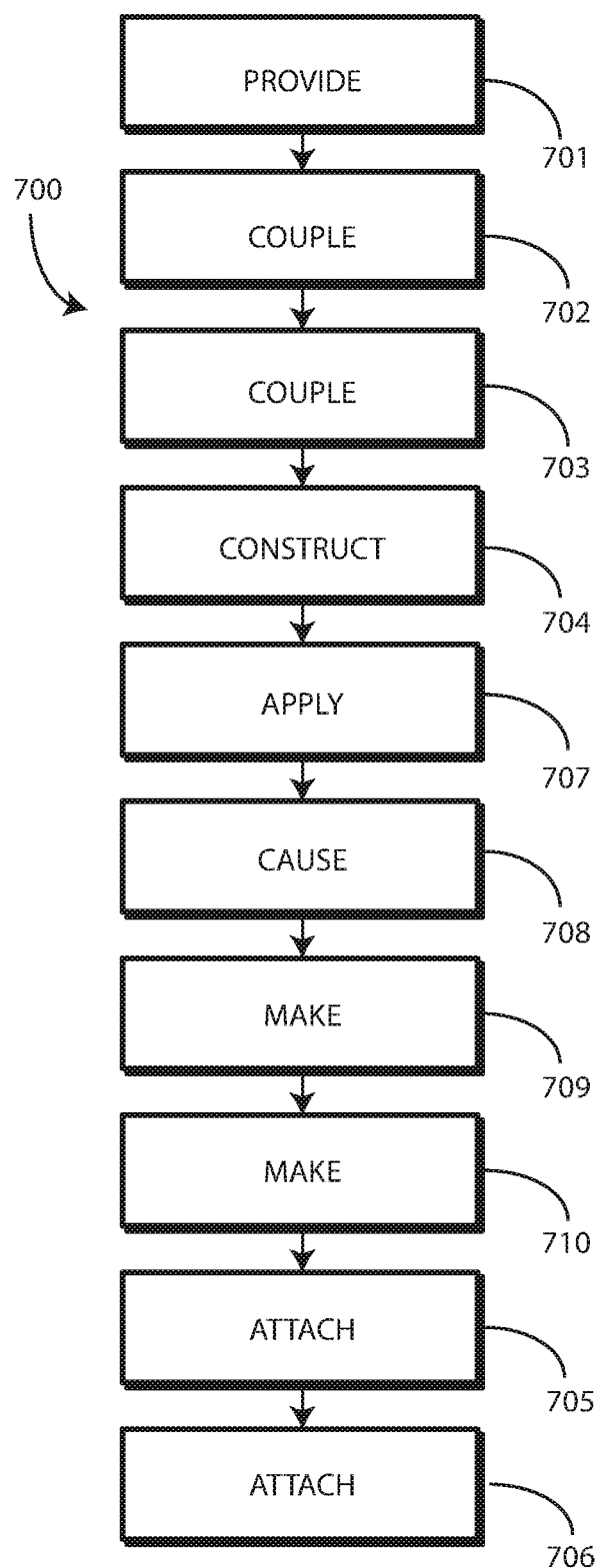
FIG. 7 illustrates an explanatory method of manufacturing an explanatory compression wrap in accordance with one or more embodiments of the disclosure.

Turning now to FIG. 7, illustrated therein is one explanatory method 700 for manufacturing a compression wrap, such as that shown in FIGS. 1-3 above. At step 701, the method 700 includes providing an elongated wrap body extending from a first end to a distal end. At step 702, the method 700 comprises coupling a fastening tab coupled to a first major face of the elongated wrap body at the first end. At step 703, the method 700 includes coupling a fastening loop coupled to the first major face of the elongated wrap body at the distal end.

At step 704, the method includes constructing a compression pad. In one embodiment, the compression pad of step 704 is disposed along a second major face of the elongated wrap body between the first end and the distal end. In one embodiment, step 704 includes causing the compression pad to have an ovular perimeter along the second major face. In one embodiment, step 704 comprises disposing the compression pad closer to the distal end of the elongated wrap body than the first end of the elongated wrap body.

At step 705, the method 700 includes attaching a first stretchable layer end of a stretchable layer to the second major face of the elongated wrap body at a first side of the compression pad. At step 706, the method 700 includes attaching a second stretchable layer end of the stretchable layer to the second major face of the elongated wrap body at a second side of the compression pad. When both step 705 and 706 are performed, this results in the stretchable layer straddling the compression pad to define a partial sleeve. This partial sleeve is completed by a portion of the elongated wrap body comprising the compression pad. The completion of the partial sleeve defines a stretchable sleeve.

In one embodiment, optional step 707 comprises applying a border material to one or both of the stretchable layer and the elongated wrap body. At optional step 708, the method can comprise causing the stretchable layer and the elongated wrap body to have a common color. For example, in one embodiment both the stretchable layer and the elongated wrap body are black. Other colors will be obvious to those of ordinary skill in the art having the benefit of this disclosure.

In one embodiment, optional step 709 comprises making the portion of the elongated wrap body comprising the compression pad wider than another portion of the elongated wrap body disposed between the first end of the elongated wrap body and the compression pad. In one embodiment, optional step 710 comprises making the elongated wrap body wider than the stretchable layer.

In the foregoing specification, specific embodiments of the present disclosure have been described. However, one of ordinary skill in the art appreciates that various modifications and changes can be made without departing from the scope of the present disclosure as set forth in the claims below. Thus, while preferred embodiments of the disclosure have been illustrated and described, it is clear that the disclosure is not so limited. Numerous modifications, changes, variations, substitutions, and equivalents will occur to those skilled in the art without departing from the spirit and scope of the present disclosure as defined by the following claims. Accordingly, the specification and figures are to be regarded in an illustrative rather than a restrictive sense, and all such modifications are intended to be included within the scope of present disclosure. The benefits, advantages, solutions to problems, and any element(s) that may cause any benefit, advantage, or solution to occur or become more pronounced are not to be construed as a critical, required, or essential features or elements of any or all the claims.

What is claimed is:

1. A compression wrap, comprising:
an elongated wrap body extending from a first end to a distal end;
a fastening tab coupled to a first major face of the elongated wrap body at the first end;
a fastening loop coupled to the first major face of the elongated wrap body at the distal end;
a compression pad disposed along a second major face of the elongated wrap body between the first end and the distal end, the compression pad defining an ovular perimeter along the second major face of the elongated wrap body; and
a stretchable layer straddling the compression pad with a first stretchable layer end coupled to the second major face of the elongated wrap body to a first side of the compression pad and a second stretchable layer end coupled to the second major face of the elongated wrap body to a second side of the compression pad such that the stretchable layer and a portion of the elongated wrap body comprising the compression pad define a stretchable sleeve, the stretchable layer defining a width that is less than another width of the portion of the elongated wrap body comprising the compression pad.

2. The compression wrap of claim 1, the stretchable sleeve disposed closer to the distal end than the first end.

3. The compression wrap of claim 2, the portion of the elongated wrap body comprising the compression pad wider than another portion of the elongated wrap body disposed between the portion of the elongated wrap body comprising the compression pad and the fastening tab.

4. The compression wrap of claim 3, the another portion of the elongated wrap insertable through the fastening loop.

5. The compression wrap of claim 4, the first major face of the elongated wrap body foldable against itself allowing the fastening tab to engage one or more loops defined by the first major face of the elongated wrap body.

6. The compression wrap of claim 3, the stretchable layer manufactured from a combination of neoprene and nylon.

7. The compression wrap of claim 1, the fastening tab comprising a hook fastener.

8. The compression wrap of claim 7, the first major face of the elongated wrap body comprising one or more loops engagable by the hook fastener.

9. The compression wrap of claim 1, wherein the elongated wrap body and the stretchable layer are manufactured from a common material.

10. The compression wrap of claim 1, wherein the elongated wrap body and the stretchable layer are manufactured from different materials.

11. The compression wrap of claim 1, wherein the compression pad is manufactured from compressible foam.

12. A compression wrap, comprising:
an elongated wrap body extending from a first end to a distal end;
a fastening tab coupled to a first major face of the elongated wrap body at the first end;
a fastening loop coupled to the first major face of the elongated wrap body at the distal end;
a compression pad disposed along a second major face of the elongated wrap body between the first end and the distal end; and
a stretchable layer straddling the compression pad with a first stretchable layer end coupled to the second major face of the elongated wrap body to a first side of the compression pad and a second stretchable layer end coupled to the second major face of the elongated wrap body to a second side of the compression pad such that the stretchable layer and a portion of the elongated wrap body comprising the compression pad define a stretchable sleeve;
wherein the elongated wrap body and the stretchable layer are manufactured from different materials.

13. The compression wrap of claim 12, the stretchable sleeve disposed closer to the distal end than the first end.

14. The compression wrap of claim 13, the portion of the elongated wrap body comprising the compression pad wider than another portion of the elongated wrap body disposed between the portion of the elongated wrap body comprising the compression pad and the fastening tab.

15. The compression wrap of claim 14, the stretchable layer manufactured from a combination of neoprene and nylon.

16. The compression wrap of claim 15, the another portion of the elongated wrap insertable through the fastening loop, the first major face of the elongated wrap body foldable against itself allowing the fastening tab to engage one or more loops defined by the first major face of the elongated wrap body.

17. The compression wrap of claim 12, the compression pad defining an ovular perimeter along the second major face of the elongated wrap body.

18. The compression wrap of claim 12, the stretchable layer defining a width that is less than another width of the portion of the elongated wrap body comprising the compression pad.

19. The compression wrap of claim 12, the fastening tab comprising a hook fastener, the first major face of the elongated wrap body comprising one or more loops engagable by the hook fastener.

20. The compression wrap of claim 12, wherein the compression pad is manufactured from compressible foam.

* * * * *